(12) United States Patent
Kimura et al.

(10) Patent No.: US 8,140,145 B2
(45) Date of Patent: Mar. 20, 2012

(54) POSITION DETECTION APPARATUS AND MEDICAL-DEVICE-POSITION DETECTION SYSTEM

(75) Inventors: Atsushi Kimura, Tokyo (JP); Akio Uchiyama, Kanagawa (JP); Ryoji Sato, Tokyo (JP)

(73) Assignee: Olympus Corporation (JP)

( * ) Notice: Subject to any disclaimer, the term of this patent is extended or adjusted under 35 U.S.C. 154(b) by 770 days.

(21) Appl. No.: 11/571,232

(22) PCT Filed: Aug. 16, 2006

(86) PCT No.: PCT/JP2006/316082
§ 371 (c)(1),
(2), (4) Date: Sep. 30, 2008

(87) PCT Pub. No.: WO2007/023716
PCT Pub. Date: Mar. 1, 2007

(65) Prior Publication Data
US 2009/0018434 A1    Jan. 15, 2009

(51) Int. Cl.
*A61B 5/05* (2006.01)
(52) U.S. Cl. ........ 600/424; 600/420; 600/422; 600/409; 324/207.11; 324/207.12; 324/207.15
(58) Field of Classification Search .................. 600/407, 600/409, 420, 422, 424, 117, 302; 324/207.11, 324/207.12, 207.15
See application file for complete search history.

(56) References Cited

U.S. PATENT DOCUMENTS

| | | | |
|---|---|---|---|
| 6,665,554 B1 * | 12/2003 | Charles et al. | 600/427 |
| 6,776,165 B2 * | 8/2004 | Jin | 128/899 |
| 7,805,269 B2 * | 9/2010 | Glossop | 702/94 |
| 2006/0119357 A1 * | 6/2006 | Alvarez et al. | 324/311 |

FOREIGN PATENT DOCUMENTS

| | | |
|---|---|---|
| JP | 06-285944 | 10/1994 |
| JP | 2001-27676 | 1/2001 |
| JP | 2004-117227 | 4/2004 |
| JP | 2005-103091 | 4/2005 |

OTHER PUBLICATIONS

JP 2001/027676 to Sadaaki—Machine Translation.*
International Search Report issued Nov. 28, 2006 in connection with corresponding application No. PCT/JP2006/316082.
*Precision Position-Detecting System Using an LC Resonant Magnetic Marker*, (Untranslated) Tokunaga, et. al., Journal of the Magnetics Society of Japan, vol. 29, No. 2, pp. 153-156, (Feb. 2005).
*Precision Position-Detecting System Using an LC Resonant Magnetic Marker*, (Translated) Tokunaga, et. al., Journal of the Magnetics Society of Japan, vol. 29, No. 2, pp. 153-156, (Feb. 2005).

* cited by examiner

*Primary Examiner* — Brian Casler
*Assistant Examiner* — Rajeev Siripurapu
(74) *Attorney, Agent, or Firm* — Ostrolenk Faber LLP

(57) ABSTRACT

A position detection apparatus and a medical-device-position detection system that have improved position detection accuracy are provided by setting high amplification for the position detection apparatus. The position detection apparatus includes a circuit that has at least one embedded coil (10*a*) and that is provided inside an object (10) to be detected; a first magnetic-field generating unit (11) for generating a first magnetic field in the region where the embedded coil (10*a*) is disposed; a magnetic-field detecting unit (5, 12) for detecting an induced magnetic field generated at the embedded coil (10*a*) by the first magnetic field; and a second magnetic-field generating unit (23) for generating a second magnetic field having a phase substantially opposite to the phase of the first magnetic field.

30 Claims, 9 Drawing Sheets

POSITION DETECTION APPARATUS AND MEDICAL-DEVICE-POSITION DETECTION SYSTEM

CROSS REFERENCE TO RELATED APPLICATION

The present application is a 35 U.S.C. §§371 national phase conversion of PCT/JP2006/316082 filed 16 Aug. 2006, which claims priority from Japanese patent application 2005-242359 filed 24 Aug. 2005, which is herein incorporated by reference. The PCT International Application was published in the Japanese language.

BACKGROUND OF THE INVENTION

1. Field of the Invention

The present invention relates to a position detection apparatus and a medial-apparatus-position detection system.

2. Description of Related Art

Recently, there has been research and development of swallowable capsule medical devices (objects to be detected), as represented by capsule endoscopes and the like, that are swallowed by a subject to enter the subject's body, where they traverse a passage in the body cavity to capture images of a target site inside the passage in the body cavity.

To guide such a capsule medical device to a predetermined position in a passage in the body cavity, currently, the position of the capsule medical device in the passage in the body cavity must be detected and a solution to guide the capsule medical device is required.

One known solution to guide the capsule medical device is to control the position of the capsule medical device by installing a magnet inside the capsule medical device and externally applying a magnetic field.

One known method of detecting the position of the capsule medical device is a magnetic position detection method. A known magnetic position detection method is a technology of determining the position of an object to be detected by externally applying a magnetic field to the object to be detected that includes an embedded coil and detecting the magnetic field generated by an induced electromotive force with an external magnetic sensor (for example, Japanese Unexamined Patent Application Publication No. HEI-6-285044 and Tokunaga, Hashi, Yabukami, Kouno, Toyoda, Ozawa, Okazaki, and Arai, "High-resolution position detection system using LC resonant magnetic marker", Magnetics Society of Japan, 2005, 29, p. 153-156.

BRIEF SUMMARY OF THE INVENTION

The above-mentioned Patent Document 1 discloses a technology of externally positioning a substantially rectangular-solid-shaped magnetic field source having three magnetic-field generating coils whose axes intersect orthogonally and positioning three magnetic-field detecting coils having magnetic-field receiving coils whose axes also intersect orthogonally inside a medial capsule. According to this technology, an induced current is generated at the magnetic-field detecting coils by an alternating magnetic field generated by the magnetic field source so as to detect the positions of the magnetic-field detecting coils, i.e., the position of the medical capsule, based on the generated induced current.

However, according to the above-described technology, the intensity of the alternating magnetic field generated by the magnetic field source and the intensity of the induced current generated at the magnetic-field detecting coils are proportional. Therefore, there is a problem in that, to improve the detection efficiency, the intensity of the alternating magnetic field has to be increased by the same extent.

In Non-Patent Document 1, a position detection system including an excitation coil for generating an alternating magnetic field, an LC resonance magnetic marker for generating an induced magnetic field by receiving the alternating magnetic field, and a detecting coil for detecting the induced magnetic field are disclosed. According to this position detection system, since the LC resonance magnetic marker resonates at a predetermined frequency depending on additional capacitance and parasitic capacitance, by setting the frequency of the alternating magnetic field to the predetermined frequency, the intensity of the induced magnetic field can be significantly increased compared to that of other frequencies, and thus, the detection efficiency increases.

However, for the system according to Non-Patent Document 1, the detecting coil captures the alternating magnetic field generated by the excitation coil, in addition to the induced magnetic field generated by the LC resonance magnetic marker.

It is known that, in a position detection process, the induced magnetic field can be detected by subtracting an alternating magnetic field measured when an induced magnetic field is not present since the induced magnetic field to be detected is a very small magnetic field compared to the above-mentioned alternating magnetic field.

This operation is carried out, for example, after an analog signal, such as the detected alternating magnetic field, is converted into a digital signal by an analog-to-digital (A/D) converter. The analog signal captured by the detection coil is input to the A/D converter after an amplification process. However, as described above, the analog signal output from the detection coil includes more signals associated with the alternating magnetic field than signals associated with the induced magnetic field.

For this reason, when the signals associated with the induced magnetic field are amplified to a level sufficient for position detection (when the gain of the amplifier is increased), there is a possibility that the amplifier will be saturated. As a result, there is a problem in that the signals associated with the induced magnetic field cannot be amplified to a sufficient level.

In general, the setting of the amplification of the amplifier is set on the basis of the intensity of the alternating magnetic field such that the amplifier does not become saturated. Therefore, there is problem in that, with respect to the signals associated with the induced magnetic field, the amplification is kept low and the position detection accuracy of the LC resonance magnetic marker, i.e., the position detection accuracy of the position detection system, is sacrificed.

The present invention has been conceived in light of the problems described above. Accordingly, it is an object of the present invention to provide a position detection apparatus and a medical-device-position detection system with improved position detection accuracy by setting high amplification for the position detection apparatus.

To achieve this object, the present invention provides the following solutions.

A first aspect of the present invention provides a position detection apparatus including a circuit provided inside an object to be detected, the circuit including at least one embedded coil; a first magnetic-field generating unit for generating a first magnetic field; a magnetic-field detecting unit for detecting an induced magnetic field generated at the embedded coil by the first magnetic field; and a second magnetic-field generating unit for generating a second magnetic field having a phase substantially opposite to the phase of the first magnetic field.

According to the first aspect, the second magnetic field having a phase substantially opposite to the phase of the first magnetic field that is generated by the second magnetic-field generating unit can cancel out the first magnetic field at the position of the magnetic-field detecting unit. In other words, the intensity of a combined magnetic field of the first magnetic field and the second magnetic field that are detected by the magnetic-field detecting unit can be minimized (for example, set to zero) and the magnetic-field detecting unit can capture only the induced magnetic field.

Therefore, for example, when the output from the magnetic-field detecting unit is amplified, high amplification can be set based on the output associated with the induced magnetic field, and the accuracy of position detection of the object to be detected can be increased.

By positioning the second magnetic-field generating unit in the vicinity of the magnetic-field detecting unit, the second magnetic field can be more easily canceled out at the position of the magnetic-field detecting unit.

According to the present invention, it is desirable that the second magnetic-field generating unit is position in the vicinity of the first magnetic-field generating unit and includes a mutually-induced-magnetic-field generating coil for generating a mutually induced magnetic field by the first magnetic field and a second magnetic-field generating coil positioned in the vicinity of the magnetic-field detecting unit, and the mutually-induced-magnetic-field generating coil and the second magnetic-field generating coil are electrically connected in series.

In this way, the mutually-induced-magnetic-field generating coil that is positioned in the vicinity of the first magnetic-field generating unit receives the first magnetic field generated at the first magnetic-field generating unit and generates a mutually induced magnetic field as a second magnetic field. The phase of the mutually induced magnetic field is opposite to that of the first magnetic field. At this time, since the mutually-induced-magnetic-field generating coil is electrically connected in series to the second magnetic-field generating coil position in the vicinity of the magnetic-field detecting unit, a second magnetic field whose phase is substantially opposite to that of the first magnetic field is generated. As a result, the second magnetic field whose phase is substantially opposite to that of the first magnetic field can be generated by a simple configuration and the intensity of the second magnetic field can be increased at the position of the magnetic-field detecting unit. Therefore, the first magnetic field can be more reliably canceled out at the position of the magnetic-field detecting unit.

According to the present invention, it is desirable that the second magnetic-field generating unit is provided with a moving mechanism for moving the position of at least one of the mutually-induced-magnetic-field generating coil and the second magnetic-field generating coil.

By providing a moving mechanism that can move the position of at least one of the mutually-induced-magnetic-field generating coil and the second magnetic-field generating coil (hereinafter, referred to as "mutually-induced-magnetic-field generating coil or the like") and adjusting the position of the mutually-induced-magnetic-field generating coil or the like, the intensity of the second magnetic field at the position of the magnetic-field detecting unit can be adjusted.

According to the above-described configuration, it is desirable that the moving mechanism moves the position of the mutually-induced-magnetic-field generating coil so as to minimize the intensity of a magnetic-field-intensity signal associated with a combined magnetic field of the first magnetic field and the second magnetic field that are output from the magnetic-field detecting unit.

In this way, since the position of the mutually-induced-magnetic-field generating coil is adjusted by the moving mechanism so as to minimize the intensity of the magnetic-field-intensity signal associated with the combined magnetic field, the intensity of the magnetic-field-intensity signal associated with the combined magnetic field of the first and second magnetic fields can be minimized at the position of the magnetic-field detecting unit.

According to the above-described configuration, it is desirable that the moving mechanism moves the position of the second magnetic-field generating coil so as to minimize the intensity of a magnetic-field-intensity signal being output from the magnetic-field detecting unit and being associated with a combined magnetic field of the first magnetic field and the second magnetic field.

In this way, since the position of the second magnetic-field generating coil is adjusted by the moving mechanism so as to minimize the intensity of the magnetic-field-intensity signal associated with the combined magnetic field, the intensity of the magnetic-field-intensity signal associated with the combined magnetic field of the first and second magnetic fields can be minimized at the position of the magnetic-field detecting unit.

According to the present invention, it is desirable that the second magnetic-field generating unit includes a phase adjusting unit for generating a signal having a substantially reversed phase from a signal for magnetic field generation, a second-magnetic-field-generating-coil driving unit for amplifying the signal, and a second-magnetic-field generating coil for generating a second magnetic field from the amplified signal that is positioned in the vicinity of the magnetic-field sensor.

In this way, since the phase adjusting unit for generating a signal having a substantially reversed phase from a signal for magnetic field generation is provided as a component, a second magnetic field having a phase substantially opposite to that of the first magnetic field can be more reliably generated, and since the second-magnetic-field-generating-coil driving unit for amplifying the signal is provided as a component, the second magnetic field can be generated with a predetermined magnetic field intensity. Therefore, a second magnetic field capable of canceling out the first magnetic field can be generated more reliably.

According to the present invention, it is desirable that the second magnetic-field generating unit includes a phase adjusting unit for generating a signal having a substantially reversed phase from a signal for magnetic field generation, a second-magnetic-field-generating-coil driving unit for amplifying the signal, and a second-magnetic-field generating coil that is positioned in the vicinity of the magnetic-field sensor and that generates a second magnetic field from the amplified signal, and it is desirable that the second-magnetic-field-generating-coil driving unit adjusts the intensity of the second magnetic field based on a magnetic-field-intensity signal output from the magnetic-field detecting unit so as to minimize the signal intensity.

In this way, since the intensity of the second magnetic field is adjusted on the basis of the above-described magnetic-field-intensity signal such that the magnetic-field-intensity signal is minimized, the intensity of the combined magnetic field of the first magnetic field and the second magnetic field can be minimized at the magnetic-field detecting unit.

According to the present invention, it is desirable that a display unit for displaying a magnetic-field-intensity signal output form the magnetic-field detecting unit.

In this way, the magnetic-field-intensity signal output from the magnetic-field sensor can be confirmed sequentially on the display unit.

A second aspect of the present invention provides a medical-device-position detection system including a medical device having a circuit having at least one embedded coil and a magnet; a first magnetic-field generating unit for generating a first magnetic field; a magnetic-field detecting unit for detecting an induced magnetic field excited at the embedded coil by the first magnetic field; and a second magnetic-field generating unit for generating a second magnetic field having a phase substantially opposite to the phase of the first magnetic field and a third magnetic field for controlling the position and orientation of the medical device by acting upon the magnet.

According to the second aspect of the present invention, since the third magnetic field acts upon the magnet so as to guide the medical device, the medical device can be guided to a predetermined position while confirming the position of the medical device.

Furthermore, since the phase of the second magnetic field is substantially opposite to the phase of the first magnetic field, the first magnetic field can be canceled out at the position of the magnetic-field detecting unit. In other words, the intensity of the combined magnetic field of the first magnetic field and the second magnetic field that are captured by the magnetic-field detecting unit can be minimized (for example, set to zero), and the magnetic-field detecting unit can capture only the induced magnetic field. Thus, the position detection accuracy can be improved.

In the position detection apparatus and the medical-device-position detection system according to the present invention, since the alternating magnetic field can be canceled out at the position of the magnetic-field sensor by a reversed-phase magnetic field whose phase is substantially opposite to the phase of the alternating magnetic field that is generated at the reversed-phase-magnetic-field generator, for example, amplification can be set high on the basis of the output associated with the induced magnetic field when amplifying the output from the magnetic-field sensor. Thus, it is advantage in that the accuracy of the position detection of the object to be detected can be improved.

Since the alternating magnetic field can be more easily canceled out at the position of the magnetic-field sensor by positioning the reversed-phase-magnetic-field generator in the vicinity of the magnetic-field sensor, the amplification of the position detection apparatus can be set high. Thus, it is advantage in that the position detection accuracy can be improved.

DETAILED DESCRIPTION OF THE INVENTION

Position Detection Apparatus

First Embodiment

A position detection apparatus according to a first embodiment of the present invention will be described below with reference to FIGS. 1 to 4.

Figure 1:
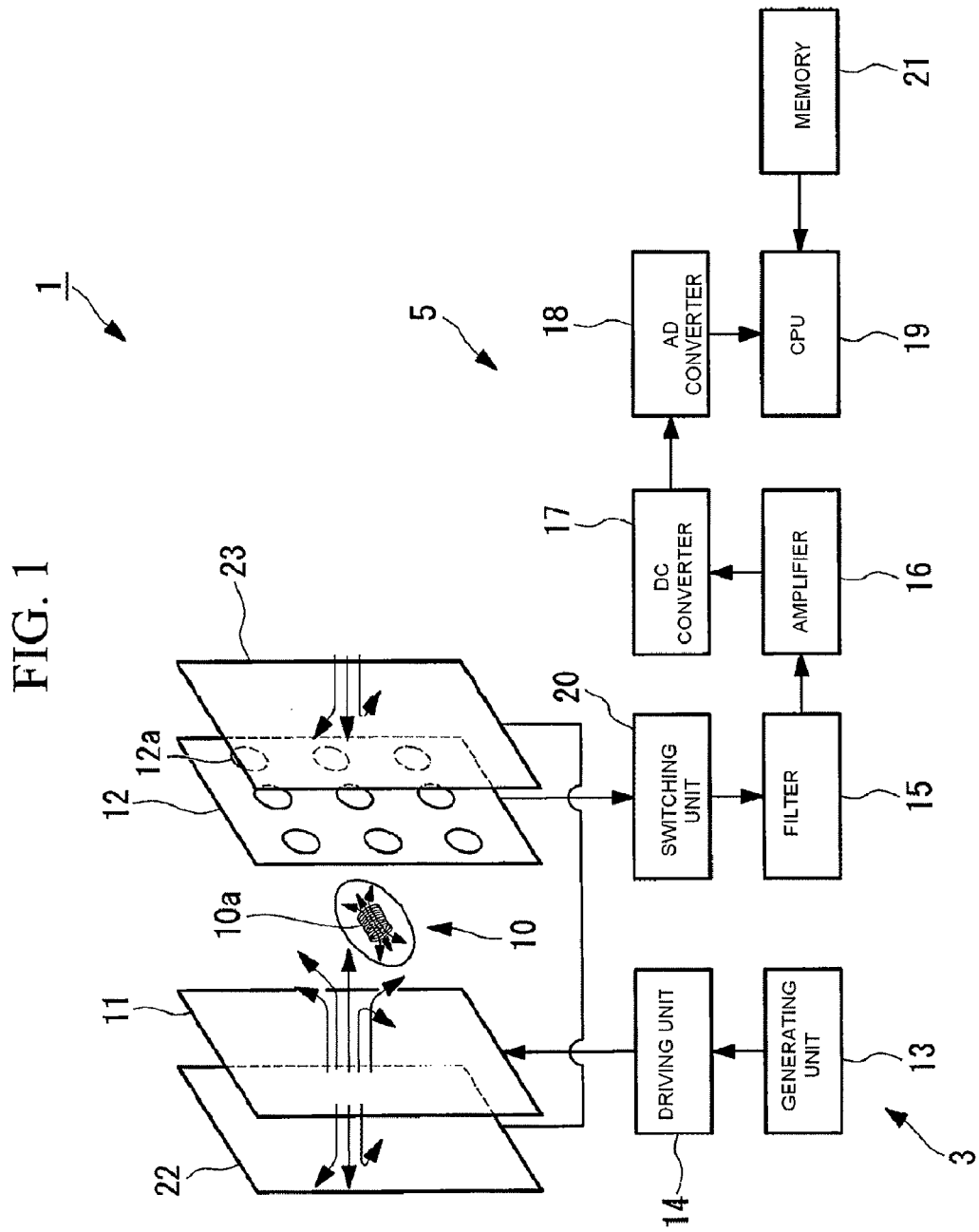
FIG. 1 is a schematic view illustrating the outline of a position detection apparatus according to a first embodiment of the present invention.

FIG. 1 is a schematic view illustrating the outline of a position detection apparatus according to the first embodiment.

As shown in FIG. 1, a position detection apparatus 1 is mainly formed of a magnetic-field generating coil (first magnetic-field generating unit) 11 that generates an alternating magnetic field (first magnetic field); a magnetic-field sensor (magnetic-field detecting unit) 12 that detects an induced magnetic field generated by an embedded coil 10a installed on an object 10 to be detected; a driving unit 3 that is used for driving control of the magnetic-field generating coil 11; a detecting unit (magnetic-field detecting unit) 5 that processes a signal output from the magnetic-field sensor 12; a reversed-phase-magnetic-field generating coil (second magnetic-field generating unit, second magnetic-field generating coil) 23 that generates a reversed-phase magnetic field (second magnetic field); and a coupled coil (second magnetic-field generating unit, mutually-induced-magnetic-field generating coil) 22.

An example of the object 10 to be detected is a capsule medical device that is put into the body of a subject to perform medical procedures.

As shown in FIG. 1, in the object 10 to be detected, an object closed circuit (not shown) including the embedded coil 10a and a capacitor having a predetermined capacity (not shown) is constructed, and an LC resonance circuit that brings about resonance at a predetermined frequency is provided.

As described above, the LC resonant circuit can be used as an object closed circuit, or if a predetermined resonance frequency can be achieved with parasitic capacitance in the embedded coil 10a, the embedded coil 10a alone, with both ends open, can form the object closed circuit.

The magnetic-field generating coil 11 is formed in a substantially planar shape and is electrically connected to the driving unit 3.

The driving unit 3 is mainly composed of a signal generating unit 13 that outputs an alternating signal having a frequency of the alternating magnetic field generated at the magnetic-field generating coil 11 and a magnetic-field-generating-coil driving unit 14 that drives the magnetic-field generating coil 11 by amplifying the alternating signal input from the signal generating unit 13.

The magnetic-field sensor 12 is constructed of a plurality of detecting coils 12a disposed in a substantially planar shape. Each of the detecting coils 12a is electrically connected to a detecting unit 5. The magnetic-field sensor 12 is disposed opposite to the magnetic-field generating coil 11, and the object 10 to be detected is interposed between the magnetic-field sensor 12 and the magnetic-field generating coil 11.

The detecting unit 5 is mainly composed of a filter 15 for cutting unwanted frequency components contained in an output signal (magnetic-field-intensity signal) from the detecting coils 12a; an amplifier 16 for amplifying the output signal from which unwanted components are cut; a DC converter 17 for converting the amplified output signal from an AC signal to a DC signal; an A/D converter 18 for converting the DC-converted output signal from an analog signal to a digital signal; and a CPU 19 for performing computational processing based on the output signal converted into a digital signal.

When a plurality of the magnetic-field sensor 12 is disposed around the object 10 to be detected, a magnetic-field-sensor switching unit 20 for selecting an output signal of a predetermined detecting coil 12a among the output signals from all detecting coils 12a is provided between the magnetic-field sensor 12 and the filter 15. By providing the magnetic-field-sensor switching unit 20, only output signals of the detecting coils 12a that are required for position detection can be selected to reduce the computational load of the CPU 19. Examples of output signals required for position detection are output signals having high signal intensity and output signals from the detecting coils 12a at positions close to the object 10 to be detected.

A memory 21 for saving an output signal acquired while the object 10 to be detected is not present is connected to the CPU 19. By arranging the memory 21, it is easier to subtract an output signal acquired while the object 10 to be detected is not present from an output signal acquired while the object 10 to be detected is present. For this reason, only an output signal associated with the induced magnetic field generated by the embedded coil 10a on the object 10 to be detected can easily be detected.

An example of the DC converter 17 is an RMS converter. However, the DC converter 17 is not limited and any known AC-DC converter may be used.

Figure 2:
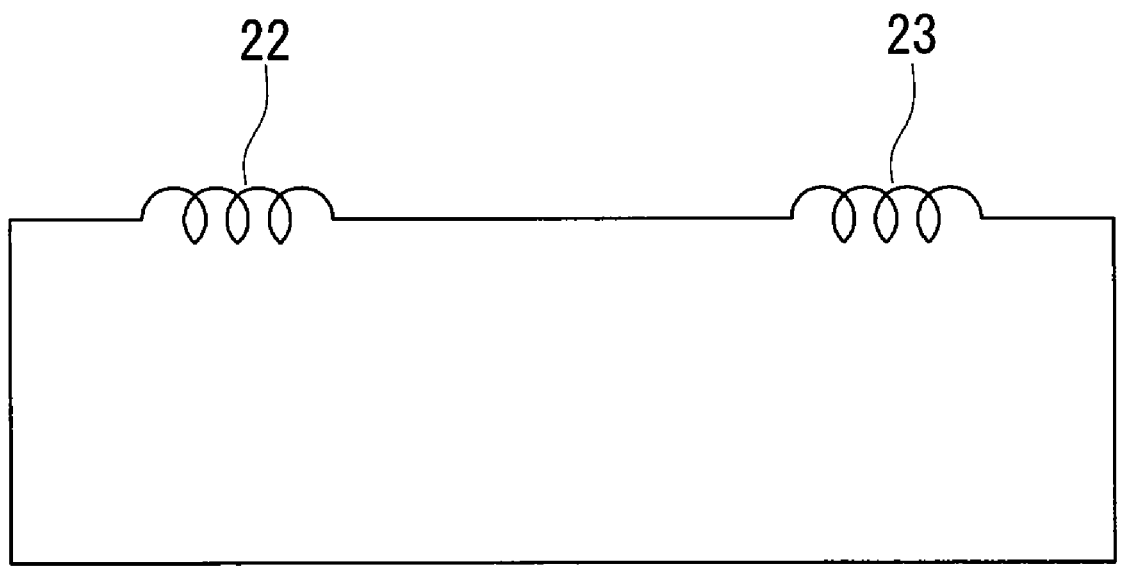
FIG. 2 is a circuit diagram showing the circuitry constituted of a coupled coil and a reversed-phase magnetic field, shown in FIG. 1.

FIG. 2 is a circuit diagram illustrating the circuitry constituted of the coupled coil and a reversed-phase-magnetic-field generating coil, as shown in FIG. 1.

The coupled coil 22 is constituted of a coil formed in a substantially planar shape, and, as shown in FIGS. 1 and 2, is electrically connected to the reversed-phase-magnetic-field generating coil 23 to constitute a closed circuit. Furthermore, as shown in FIG. 1, the coupled coil 22 is disposed in such a manner as to be magnetically coupled with the magnetic-field generating coil 11 by being positioned opposite to the magnetic-field generating coil 11 and in the vicinity thereof. Moreover, the coupled coil 22 is disposed at a position opposite to the object 10 to be detected with respect to the magnetic-field generating coil 11.

The reversed-phase-magnetic-field generating coil 23 is constituted of a coil formed in a substantially planar shape, and as shown in FIGS. 1 and 2, is electrically connected in series with the coupled coil 22 to constitute a closed circuit. Furthermore, as shown in FIG. 1, the reversed-phase-magnetic-field generating coil 23 is disposed in such a manner as to be electrically coupled with the magnetic-field sensor 12 by being positioned opposite to the magnetic-field sensor 12 and in the vicinity thereof. Moreover, the reversed-phase-magnetic-field generating coil 23 is disposed at a position opposite to the object 10 to be detected with respect to the magnetic-field sensor 12, which is interposed between the reversed-phase-magnetic-field generating coil 23 and the object 10 to be detected.

Figure 3:
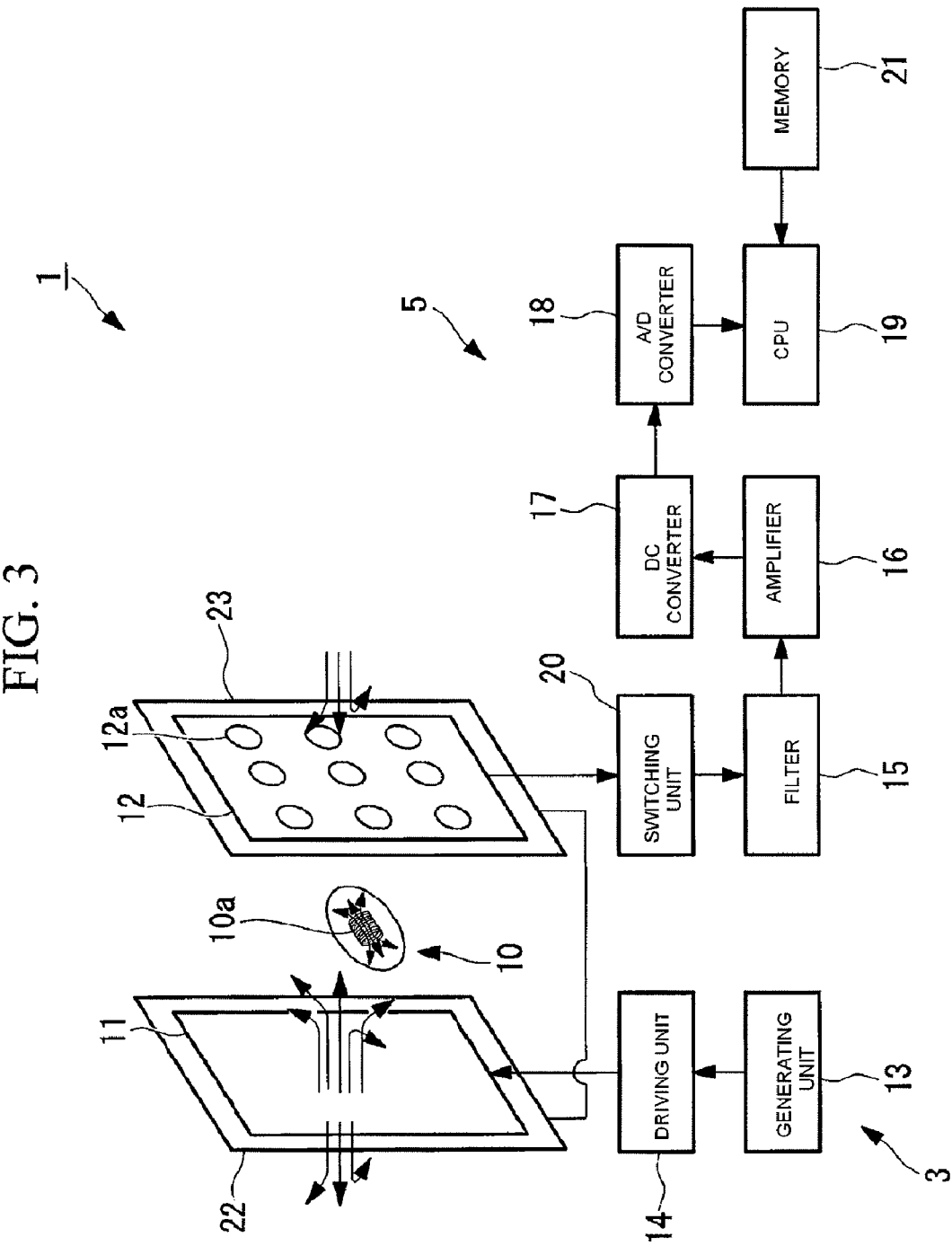
FIG. 3 illustrates other positional relationships of the coupled coil and a magnetic-field generating coil, and the reversed-phase magnetic field and a magnetic-field sensor, which are shown in FIG. 1.

The positional relationship between the coupled coil 22 and the magnetic-field generating coil 11 or the positional relationship between the reversed-phase-magnetic-field generating coil 23 and the magnetic-field sensor 12 can be switched. Furthermore, if the coupled coil 22 has an air core and is shaped so as to accommodate therein the magnetic-field generating coil 11, then the coupled coil 22 and the magnetic-field generating coil 11 may be arranged on substantially the same flat surface, as shown in FIG. 3. In addition, if the reversed-phase-magnetic-field generating coil 23 has an air core and is shaped so as to accommodate therein the magnetic-field sensor 12, then the reversed-phase-magnetic-field generating coil 23 and the magnetic-field sensor 12 may be arranged on substantially the same flat surface.

The operation of the position detection apparatus 1 with the above-described structure will now be described.

First, at the driving unit 3, as shown in FIG. 1, an AC signal having a predetermined frequency is generated in the signal generating unit 13, and the AC signal is output to the magnetic-field-generating-coil driving unit 14. The magnetic-field-generating-coil driving unit 14 amplifies the input AC signal to a predetermined intensity. The amplified AC signal is output to the magnetic-field generating coil 11. The magnetic-field generating coil 11 forms an alternating magnetic field therearound as a result of the AC signal being supplied.

When the magnetic flux of the alternating magnetic field intersects the object 10 to be detected, a resonant current with a predetermined frequency is induced in the object closed circuit having the embedded coil 10a installed therein. When a resonant current is induced in the object closed circuit, it causes the embedded coil 10a to form therearound an induced magnetic field having a predetermined frequency.

Since the magnetic fluxes of the above-described alternating magnetic field and the induced magnetic field intersect the detecting coils 12a of the magnetic-field sensor 12, the detecting coils 12a capture a magnetic flux generated by adding the magnetic fluxes of both the magnetic fields and generate an output signal that is an induced current based on a change in the intersecting magnetic fluxes. An output signal of each detecting coils 12a is output to the detecting unit 5.

In the detecting unit 5, the output signal that has been input is first input to the magnetic-field-sensor switching unit 20. The magnetic-field-sensor switching unit 20 passes only an output signal used for position detection of the object 10 to be detected therethrough and cuts out other output signals.

Examples of a method of selecting an output signal include selecting output signals with high signal intensity, outputting signals from the detecting coils 12a positioned near the object 10 to be detected, or the like.

Only an output signal used for position detection may be selected by arranging the magnetic-field-sensor switching unit 20 between the magnetic-field sensor 12 and the filter 15, as described above. Alternatively, by causing the magnetic-field-sensor switching unit 20 to switch the connection among a plurality of detecting coils 12a, the output signals from all detecting coils 12a may be input to the detection section 5 in a time-division manner. Furthermore, by connecting the line between the filter 15 and the A/D converter 18 to a plurality of detecting coils 12a, it is not necessary to use the magnetic-field-sensor switching unit 20 or select an output signal. Thus, no particular restrictions are applied.

The selected output signal is input to the filter 15, and frequency components in the output signal that are not used for position detection, for example, low-frequency components, are removed. The output signal from which unwanted components are removed is input to the amplifier 16 and is then amplified so as to have an input level appropriate for the A/D converter 18 downstream thereof.

The amplified output signal is input to the DC converter 17, and the output signal, which is an AC signal, is converted into a DC signal. Thereafter, the output signal is input to the A/D converter 18, and the output signal, which is an analog signal, is converted into a digital signal.

The output signal converted into a digital signal is input to the CPU 19. On the other hand, the output signal acquired from the memory 21 connected to the CPU 19 while the object 10 to be detected is not present is input to the CPU 19.

In the CPU 19, an output signal associated with the induced magnetic field is obtained by calculating the difference between both the output signals that have been input, and computation for identifying the position of the embedded coil 10a, namely the position of the object 10 to be detected, is carried out based on the obtained output signal associated with the induced magnetic field. For the computation for identifying the position, a known computation method can be used, and no particular restrictions are applied.

The operation of the coupled coil 22 and the reversed-phase-magnetic-field generating coil 23, which are the main subject matters of the present invention, will now be described.

Since the coupled coil 22 is positioned in a matter such as to be magnetically coupled with the magnetic-field generating coil 11, the magnetic flux of the alternating magnetic field generated by the magnetic-field generating coil 11 passes through the coupled coil 22. When the intensity of the magnetic field of the alternating magnetic field varies, an induced electromotive force is generated in the coupled coil 22, i.e., an electromotive force that forms a magnetic field having a direction in which variations in the magnetic field intensity are cancelled out, namely, a reversed-phase magnetic field with a phase opposite to that of the above-described alternating magnetic field.

Since the coupled coil 22 and the reversed-phase-magnetic-field generating coil 23 are electrically connected in series to form a closed circuit, an induced current based on the induced electromotive force generated at the coupled coil 22 is also applied to the reversed-phase-magnetic-field generating coil 23.

When the induced current is applied to the reversed-phase-magnetic-field generating coil 23, the reversed-phase magnetic field is generated around the reversed-phase-magnetic-field generating coil.

The distributions of the magnetic field intensities of the magnetic fields generated by the magnetic-field generating coil 11, the coupled coil 22, and the reversed-phase-magnetic-field generating coil 23 will now be described.

Figure 4:
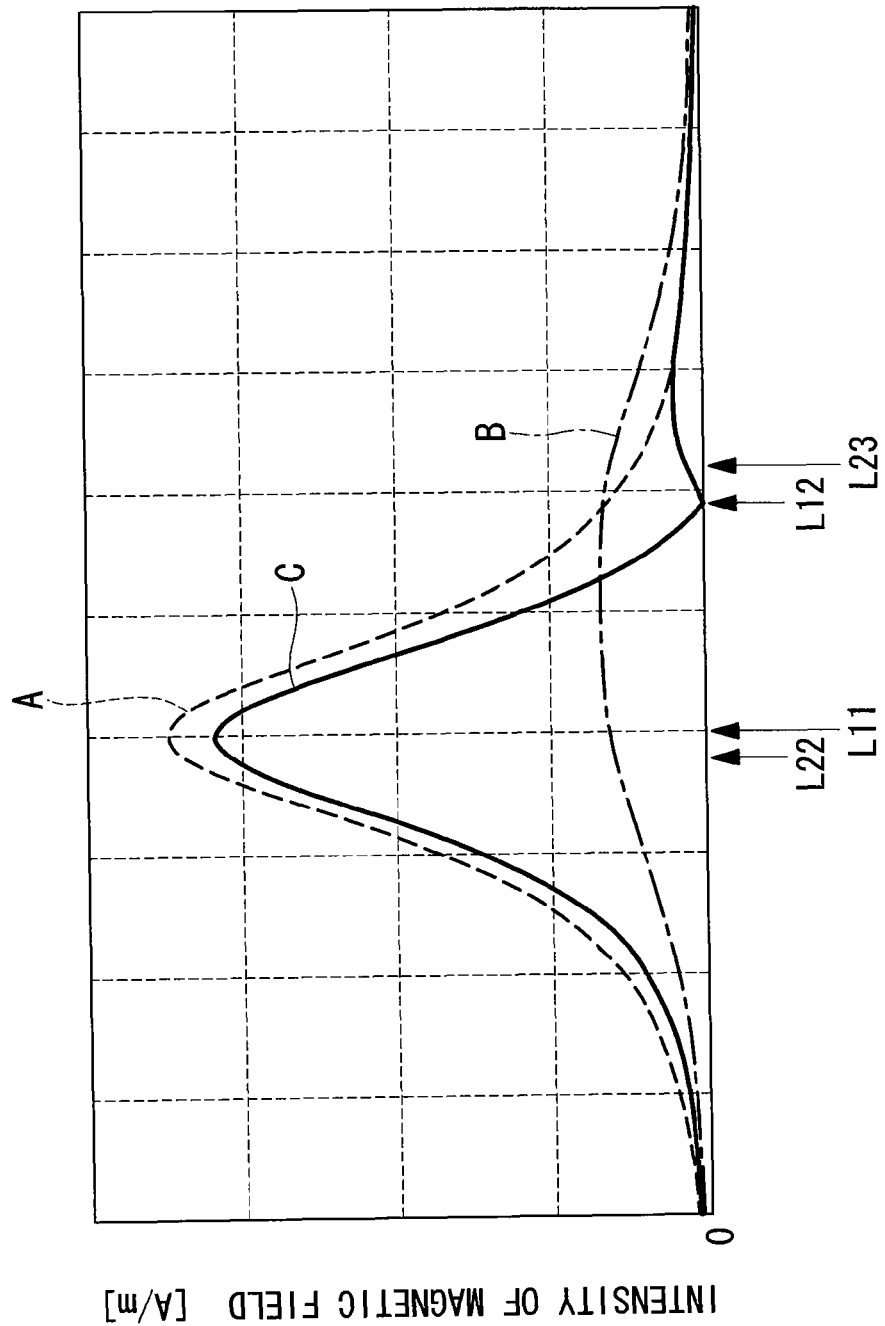
FIG. 4 illustrates the intensity of the magnetic field viewed from the side of a position measurement device shown in FIG. 1.

FIG. 4 illustrates the distributions of the magnetic fields in FIG. 1 viewed from the side of the position detection apparatus 1. The intensity distribution of the alternating magnetic field generated by the magnetic-field generating coil 11, as represented by a dotted line A in FIG. 4, is such that the intensity is maximized at a position L11 where the magnetic-field generating coil 11 is disposed, and the intensity decreases away from this position.

The intensity distribution of the reversed-phase magnetic field generated by the coupled coil 22 and the reversed-phase-magnetic-field generating coil 23, as represented by a dashed dotted line B in FIG. 4, is such that the intensity is maximized between a position L22 where the coupled coil 22 is disposed and a position L23 where the reversed-phase-magnetic-field generating coil 23 is disposed, and the intensity decreases away from L22 and L23 (left of L22 and right of L23, in FIG. 4). As shown in FIG. 4, the intensity of the reversed-phase magnetic field is lower than the intensity of the alternating magnetic field and the phase thereof is a substantially reversed phase of the alternating magnetic field.

The intensity distribution of the combined magnetic field of the above-described alternating magnetic field and revered-phase magnetic field, as represented by a solid line C in FIG. 4, is such that the intensity is maximized at the position L11 where the magnetic-field generating coil 11 is disposed, and the intensity is substantially zero at a position L12 where the magnetic-field sensor 12 is disposed, which is a position closer to the coupled coil 22 than the position L23 where the reversed-phase-magnetic-field generating coil 23 is disposed. Since the phase of the reversed-phase magnetic field is opposite to the phase of the alternating magnetic field, these magnetic fields cancel out each other.

Therefore, the phase of the combined magnetic field and the phase of the alternating magnetic field are the same on the side closer to the position L11, where the magnetic-field generating coil 11 is disposed than the position L12, whereas the phase of the combined magnetic field is opposite to the phase of the reversed-phase magnetic field on the side closer to the position L23, where the reversed-phase-magnetic-field generating coil 23 is disposed.

The position L22, where the coupled coil 22 is disposed, to the position L23, where the reversed-phase-magnetic-field generating coil 23 is disposed, may be determined such that the output of the magnetic-field sensor 12 is minimized or set to substantially zero by measuring the combined magnetic field intensity in advance or such that the output is minimized or set to substantially zero by observing the output of the magnetic-field sensor 12. The positions are not particularly limited.

According to the above-described structure, the above-described alternating magnetic field can be canceled out at the position of the magnetic-field sensor 12 by the above-described reversed-phase magnetic field generated by the coupled coil 22 and the reversed-phase-magnetic-field generating coil 23. In other words, as shown in FIG. 4, since the intensity of the combined magnetic field of the alternating magnetic field and the reversed-phase magnetic field captured by the detecting coils 12a of the magnetic-field sensor 12 can be minimized or set to substantially zero, the detecting coils 12a can capture only the above-described induced magnetic field.

Therefore, when the output signals from the detecting coils 12a are amplified at the amplifier 16, the level of amplification can be set high based on the output signal associated with the induced magnetic field, and the position detection accuracy of the object 10 to be detected can be improved.

By positioning the reversed-phase-magnetic-field generating coil 23 in the vicinity of the magnetic-field sensor 12, the alternating current can be easily canceled out at the position of the magnetic-field sensor 12.

By positioning the coupled coil 22 in the vicinity of the magnetic-field generating coil 11 and magnetically coupling the coupled coil 22 to the magnetic-field generating coil, an induced electromotive force that forms a reversed-phase magnetic field having a phase substantially opposite to the phase of the alternating magnetic field can be generated at the coupled coil 22. By using the reversed-phase-magnetic-field generating coil 23 that is electrically connected to the coupled coil 22 in series, the alternating magnetic field can be more reliably canceled out at the magnetic-field sensor 12.

As described above, the reversed-phase-magnetic-field generating coil 23 that is a special coil for generating a reversed-phase magnetic field may be disposed. Alternatively, for example, when a magnetic-field generating coil used for guiding the object 10 to be detected is provided, the position and orientation of the magnet installed in the object 10 to be detected is controlled by the magnetic field (third magnetic field) generated by the magnetic-field generating coil, and the position and orientation of the object 10 to be detected is controlled, so long as the magnetic-field generating coil used for orientation control is connected as shown in FIG. 2, the magnetic-field generating coil used for orientation control may also be used as a reversed-phase-magnetic-field generating device.

For example, so long as an opposing coil is disposed in a manner such as to satisfy Helmholtz conditions and a low-impedance driving device is connected, the same functions as those according to the first embodiment may be achieved.

As described above, the position detection apparatus 1 may include only a closed circuit including at least the embedded coil 10*a* inside the object 10 to be detected or, depending on the usage, may be used as an image-acquisition unit formed of a CCD and a CMOS for imaging the body cavity of the patient or a capsule medical device in which a container for holding medication to be received by the patient is installed, and no particular restrictions are applied.

The object 10 to be detected may be provided as a tubular medical device, such as a catheter or an endoscope, and a closed circuit including the embedded coil 10*a* may be installed at substantially the tip thereof or at an intermediate section thereof.

Second Embodiment

A position detection apparatus according to a second embodiment of the present invention will be described below with reference to FIG. 5.

The basic configuration of the position detection apparatus according to this embodiment is the same as that in the first embodiment; however, the structures of the reversed-phase-magnetic-field generating coil and the periphery thereof are different from those in the first embodiment. Thus, in this embodiment, only the structures of the reversed-phase-magnetic-field generating coil and the periphery thereof shall be described with reference to FIG. 5, and the description of the structures of other components shall be omitted.

Figure 5:
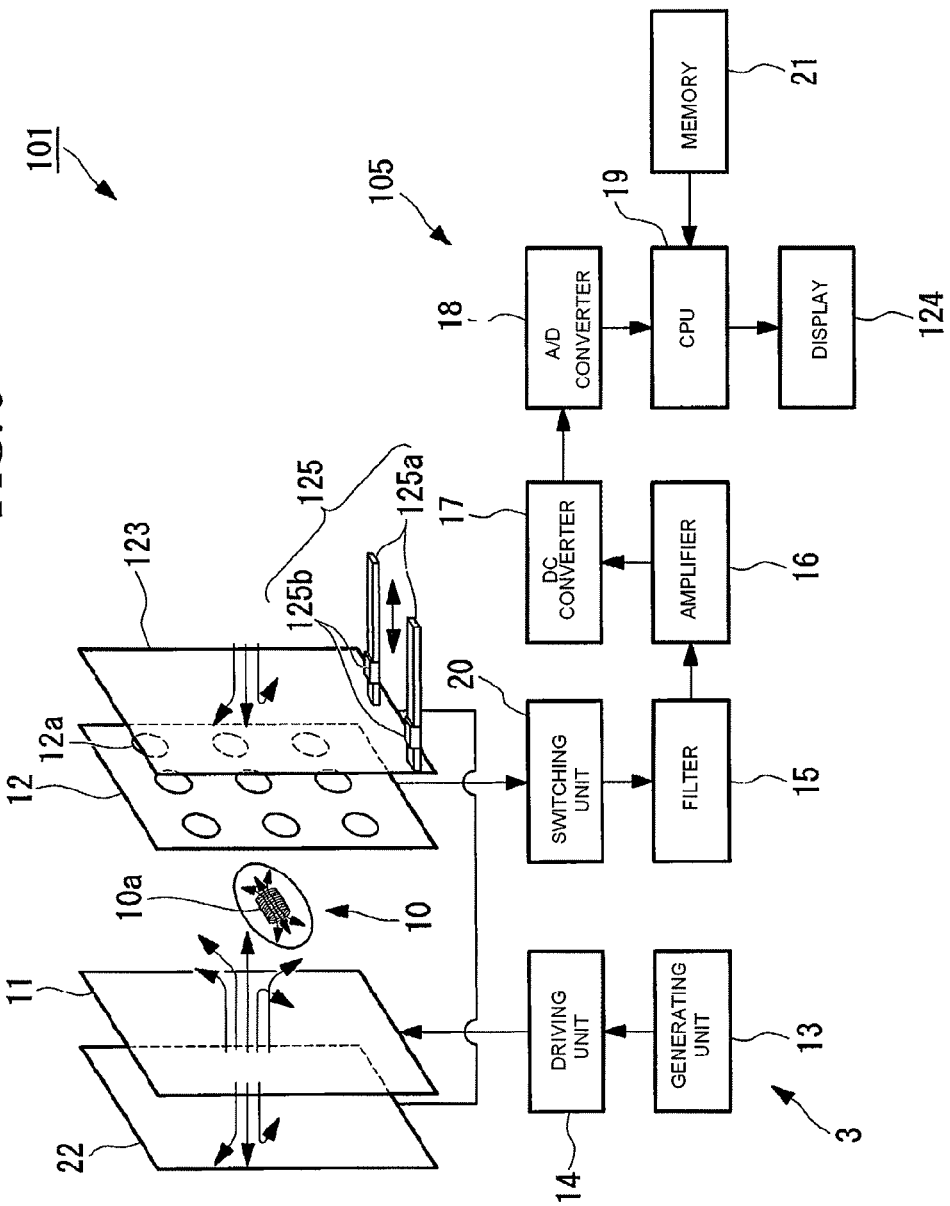
FIG. 5 is a schematic view illustrating the outline of a position detection apparatus according to a second embodiment of the present invention.

FIG. 5 is a schematic view illustrating the outline of the position detection apparatus according to this embodiment.

The same components as those in the first embodiment are denoted with the same reference numerals, and thus will not be described.

As shown in FIG. 5, a position detection apparatus 101 is mainly formed of a magnetic-field generating coil 11 that generates an alternating magnetic field; a magnetic-field sensor 12 that detects an induced magnetic field generated by an embedded coil 10*a* installed on an object 10 to be detected; a driving unit 3 that is used for driving control of the magnetic-field generating coil 11; a detecting unit (magnetic-field detecting unit) 105 that processes a signal output from the magnetic-field sensor 12; a reversed-phase-magnetic-field generating coil (second magnetic-field generating unit, second magnetic-field generating coil) 123 that generates a reversed-phase magnetic field; and a coupled coil (second magnetic-field generating unit, mutually-induced-magnetic-field generating coil) 22 that is electrically connected to the reversed-phase-magnetic-field generating coil 123.

The detecting unit 105 is mainly composed of a filter 15 for cutting unwanted frequency components contained in an output signal from the detecting coils 12*a*; an amplifier 16 for amplifying the output signal from which unwanted components are cut; a DC converter 17 for converting the amplified output signal from an AC signal to a DC signal; an A/D converter 18 for converting the DC-converted output signal from an analog signal to a digital signal; and a CPU 19 for performing computational processing based on the output signal converted into a digital signal.

When a plurality of the magnetic-field sensor 12 is disposed around the object 10 to be detected, a magnetic-field-sensor switching unit 20 for selecting an output signal of a predetermined detecting coil 12*a* among the output signals from all detecting coils 12*a* is provided.

A memory 21 for saving an output signal acquired while the object 10 to be detected is not present and a display unit 124 for displaying the magnetic field intensity captured by the magnetic-field sensor 12 as a numerical value or a graph are connected to the CPU 19. By providing the display unit 124, magnetic-field-intensity signals output from the magnetic-field sensor 12 can be confirmed sequentially.

The reversed-phase-magnetic-field generating coil 123 is constituted of a coil formed in a substantially planar shape, and, as shown in FIG. 5, is electrically connected to the coupled coil 22 to constitute a closed circuit. Furthermore, as shown in FIG. 5, the reversed-phase-magnetic-field generating coil 123 is disposed opposite to the magnetic-field sensor 12, and the magnetic-field sensor 12 is interposed between the object 10 to be detected and the reversed-phase-magnetic-field generating coil 123.

At the lower edge of the reversed-phase-magnetic-field generating coil 123 a moving mechanism 125 for supporting the reversed-phase-magnetic-field generating coil 123 in a manner such that the reversed-phase-magnetic-field generating coil 123 is movable towards or away from the magnetic-field sensor 12. The moving mechanism 125 is mainly composed of a pair of moving rails 125*a* positioned substantially orthogonal to the surface of the magnetic-field sensor 12 and supporting parts 125*b* disposed such that they are slidable on the moving rails 125*a*. The supporting parts 125*b* hold the lower edge of the reversed-phase-magnetic-field generating coil 123 by grips.

As described above, as a moving mechanism, a description has been given of an embodiment of the moving mechanism 125 constituted of the moving rails 125*a* and the supporting parts 125*b*; however, the moving mechanism 125 is not limited to being constituted of a combination of the moving rails 125*a* and the supporting parts 125*b*, and other known moving mechanisms may be used.

The operation of the position detection apparatus 101 with the above-described structure will now be described.

The steps of generating an alternating magnetic field around the object 10 to be detected, detecting an induced magnetic field generated at the embedded coil 10*a*, and determining the position of the object 10 to be detected by the CPU 19 are the same as those in the first embodiment. Thus, descriptions thereof shall be omitted.

An output signal associated with a combined magnetic field input to the CPU 19 is output to the display unit 124. The display unit 124 displays the intensity of the output signal that is input and that is associated with the combined magnetic field as a numerical value or a graph.

The position of the reversed-phase-magnetic-field generating coil 123 is adjusted by the moving mechanism 125 based on the intensity of the output signal associated with the combined magnetic field that is displayed on the display unit 124 such that the intensity is minimized or set to substantially zero. More specifically, the reversed-phase-magnetic-field generating coil 123 is moved, together with the supporting parts 125*b* on the moving rails 125*a*, towards or away from the magnetic-field sensor 12 while maintaining the direction of the central axis.

According to the above-described structure, by providing the moving mechanism 125 that can move the position of the reversed-phase-magnetic-field generating coil 123 and by adjusting the position of the reversed-phase-magnetic-field generating coil 123, the intensity of the combined magnetic field at the position of the magnetic-field sensor 12 can be adjusted to a minimum value or substantially zero.

Since the position of the reversed-phase-magnetic-field generating coil 123 is changed based on the output signal associated with the combined magnetic field displayed on the display unit 124 such that the output signal is minimized or set to substantially zero, the intensity of the combined magnetic field at the position of the magnetic-field sensor 12 can be reliably set to a minimum value or substantially zero.

As described above, the reversed-phase-magnetic-field generating coil 123 may be provided with the moving mechanism 125, and the reversed-phase-magnetic-field generating coil 123 may be movable; the coupled coil 22 may be provided with the moving mechanism 125, and the coupled coil 22 may be movable; or the coupled coil 22 and the reversed-phase-magnetic-field generating coil 123 both may be movable. Thus, no particular restrictions are applied.

Third Embodiment

A position detection apparatus according to a third embodiment of the present invention will be described below with reference to FIG. 6.

The basic configuration of the position detection apparatus according to this embodiment is the same as that in the second embodiment; however, the structures of the reversed-phase-magnetic-field generating coil and the periphery thereof are different from those in the second embodiment. Thus, in this embodiment, only the structures of the reversed-phase-magnetic-field generating coil and the periphery thereof shall be described with reference to FIG. 6, and the description of the structures of other components shall be omitted.

Figure 6:
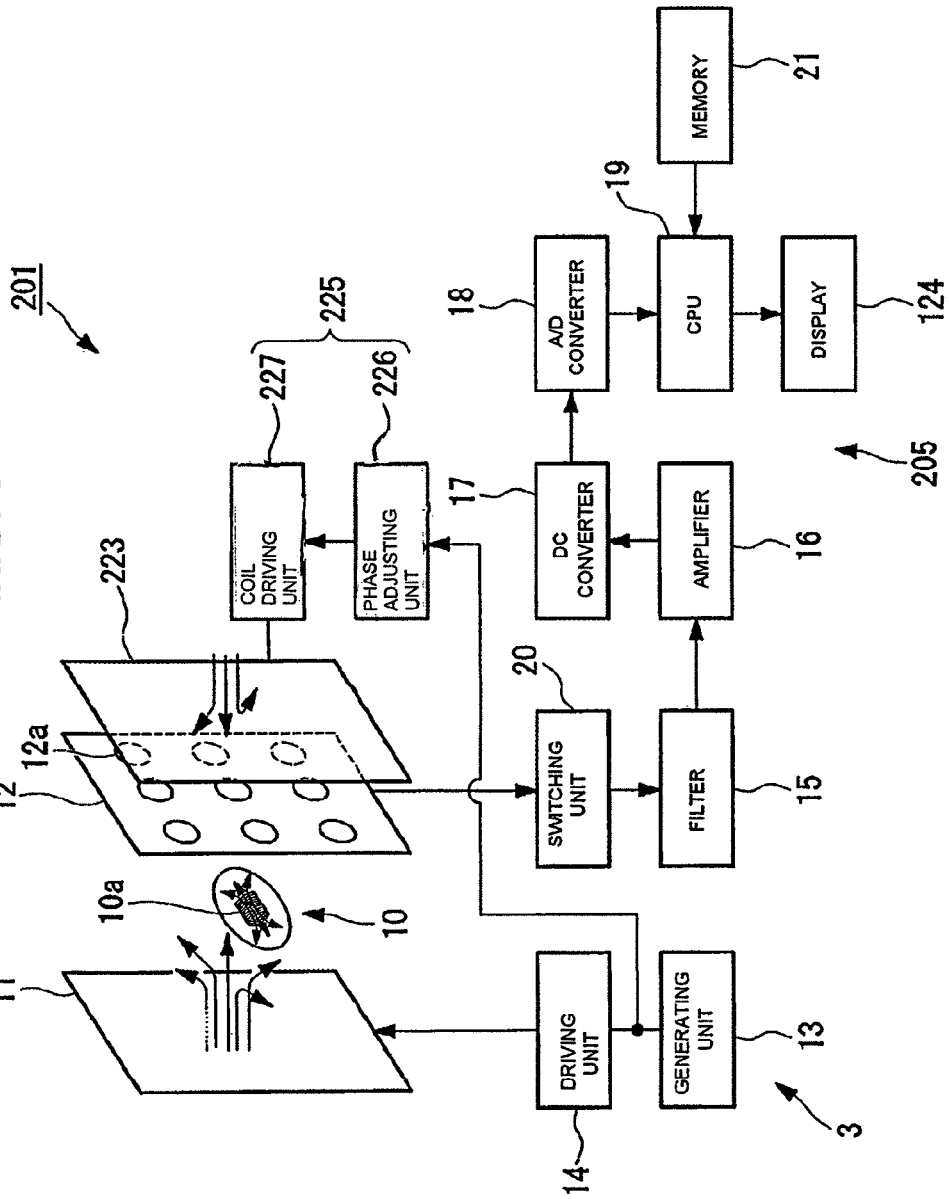
FIG. 6 is a schematic view illustrating the outline of a position detection apparatus according to a third embodiment of the present invention.

FIG. 6 is a schematic view illustrating the outline of the position detection apparatus according to this embodiment.

The same components as those in the second embodiment are denoted with the same reference numerals, and thus will not be described.

As shown in FIG. 6, a position detection apparatus 201 is mainly formed of a magnetic-field generating coil 11 that generates an alternating magnetic field; a magnetic-field sensor 12 that detects an induced magnetic field generated by an embedded coil 10*a* installed on an object 10 to be detected; a driving unit 3 that is used for driving control of the magnetic-field generating coil 11; a detecting unit 105 that processes a signal output from the magnetic-field sensor 12; and a reversed-phase-magnetic-field generating coil (second magnetic-field generating unit, second magnetic-field generating coil) 223 that generates a reversed-phase magnetic field.

The reversed-phase-magnetic-field generating coil 223 is constituted of a coil formed in a substantially planar shape, and as shown in FIG. 6, is electrically connected with a control unit (second magnetic-field generating unit) 225. Furthermore, as shown in FIG. 6, the reversed-phase-magnetic-field generating coil 223 is positioned opposite to the magnetic-field sensor 12 and is disposed such that the magnetic-field sensor 12 is interposed between the object 10 to be detected and the reversed-phase-magnetic-field generating coil 223.

The control unit 225 is mainly formed of a phase adjusting unit 226 for receiving an output from the signal generating unit 13 and a reversed-phase-magnetic-field-generating-coil driving unit (second magnetic-field-generating-coil driving unit) 227 for receiving an output from the phase adjusting unit 226.

The phase adjusting unit 226 is configured to generate a reversed-phase signal having a substantially reversed phase based on an AC signal input from a signal generating unit 13. The reversed-phase-magnetic-field-generating-coil driving unit 227 is configured to amplify the input reversed-phase signal to a predetermined intensity, that is to carry out amplitude adjustment. The amplified reversed-phase signal is output to the reversed-phase-magnetic-field generating coil 223.

The operation of the position detection apparatus 201 with the above-described structure will now be described.

The steps of generating an alternating magnetic field around the object 10 to be detected, detecting an induced magnetic field generated at the embedded coil 10*a*, and determining the position of the object 10 to be detected by the CPU 19 are the same as those in the first embodiment. Thus, descriptions thereof shall be omitted.

An output signal associated with a combined magnetic field input to the CPU 19 is output to the display unit 124. The display unit 124 displays the intensity of the output signal that is input and that is associated with the combined magnetic field as a numerical value or a graph.

The amplification of the reversed-phase-magnetic-field-generating-coil driving unit 227 is adjusted based on the intensity of the output signal associated with the combined magnetic field that is displayed on the display unit 124 such that the intensity is minimized or set to substantially zero. When the intensity of the reversed-phase signal supplied to the reversed-phase-magnetic-field generating coil 223 changes, the intensity of the reversed-phase magnetic field generated by the reversed-phase-magnetic-field generating coil 223 also changes. Therefore, a reversed-phase magnetic field having an intensity that cancels out the alternating magnetic field can be generated.

According to the configuration described above, since a reversed-phase signal having a substantially reversed phase is generated from the AC current used for generating the alternating magnetic field at the phase adjusting unit 226, a magnetic field having a phase substantially opposite to that of the alternating magnetic field can be generated more reliably. Since the reversed-phase signal is amplified by a predetermined amplification at the reversed-phase-magnetic-field-generating-coil driving unit 227, a reversed-phase magnetic field having an intensity that can cancel out the alternating magnetic field can be generated at a predetermined position. Therefore, at the position of the magnetic-field sensor 12, a reversed-phase magnetic field that can cancel out the alternating magnetic field more reliably can be generated.

By positioning the reversed-phase-magnetic-field generating coil 223 in the vicinity of the magnetic-field sensor 12, the alternating magnetic field can be more easily canceled out at the position of the magnetic-field sensor 12.

Fourth Embodiment

A position detection apparatus according to a fourth embodiment of the present invention will be described below with reference to FIG. 7.

The basic configuration of the position detection apparatus according to this embodiment is the same as that in the third embodiment; however, the structures of the reversed-phase-magnetic-field generating coil and the periphery thereof are different from those in the third embodiment. Thus, in this embodiment, only the structures of the reversed-phase-magnetic-field generating coil and the periphery thereof shall be described with reference to FIG. 7, and the description of the structures of other components shall be omitted.

Figure 7:
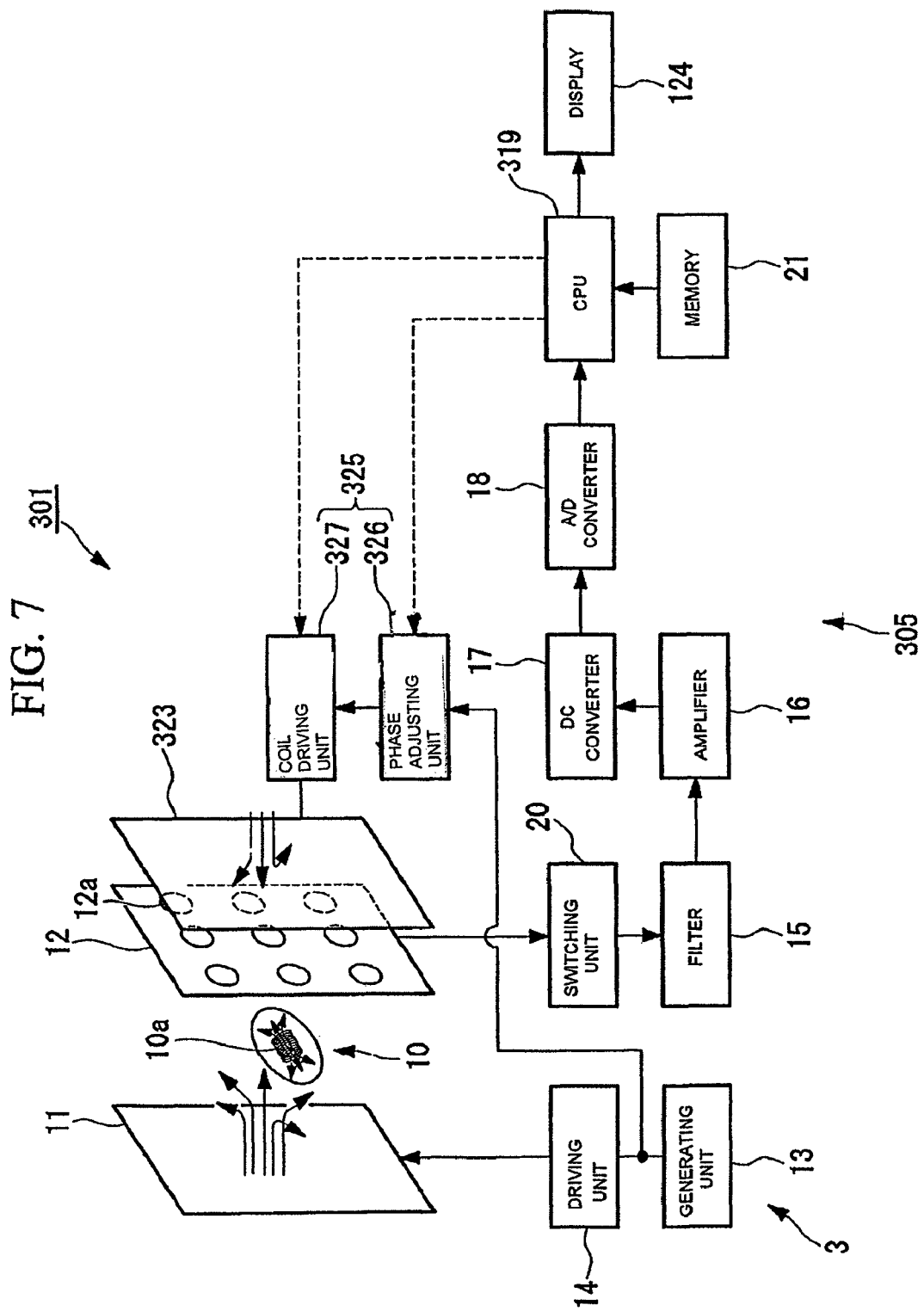
FIG. 7 is a schematic view illustrating the outline of a position detection apparatus according to a fourth embodiment of the present invention.

FIG. 7 is a schematic view illustrating the outline of the position detection apparatus according to this embodiment.

The same components as those in the third embodiment are denoted with the same reference numerals, and thus will not be described.

As shown in FIG. 7, a position detection apparatus 301 is mainly formed of a magnetic-field generating coil 11 that generates an alternating magnetic field; a magnetic-field sensor 12 that detects an induced magnetic field generated by an embedded coil 10a installed on an object 10 to be detected; a driving unit 3 that is used for driving control of the magnetic-field generating coil 11; a detecting unit (magnetic-field detecting unit) 305 that processes a signal output from the magnetic-field sensor 12; and a reversed-phase-magnetic-field generating coil (second magnetic-field generating unit, second magnetic-field generating coil) 323 that generates a reversed-phase magnetic field.

The detecting unit 305 is mainly composed of a filter 15 for cutting unwanted frequency components contained in an output signal from the detecting coils 12a; an amplifier 16 for amplifying the output signal from which unwanted components are cut; a DC converter 17 for converting the amplified output signal from an AC signal to a DC signal; an A/D converter 18 for converting the DC-converted output signal from an analog signal to a digital signal; and a CPU 319 for performing computational processing based on the output signal converted into a digital signal. The CPU 319 is configured to output control signals to a phase adjusting unit and a reversed-phase-magnetic-field-generating-coil driving unit, described below.

The reversed-phase-magnetic-field generating coil 323 is constituted of a coil formed in a substantially planar shape, and as shown in FIG. 7, is electrically connected with a control unit (second magnetic-field generating unit) 325. Furthermore, as shown in FIG. 7, the reversed-phase-magnetic-field generating coil 323 is positioned opposite to the magnetic-field sensor 12 and is disposed such that the magnetic-field sensor 12 is interposed between the object 10 to be detected and the reversed-phase-magnetic-field generating coil 223.

The control unit 325 is mainly formed of a phase adjusting unit 326 for receiving an output from the signal generating unit 13 and a reversed-phase-magnetic-field-generating-coil driving unit (second magnetic-field-generating-coil driving unit) 327 for receiving an output from the phase adjusting unit 326.

The phase adjusting unit 326 is configured to generate a reversed-phase signal having a phase misaligned from a phase of an AC signal based on the AC signal input from a signal generating unit 13 and the control signal input from the CPU 319. The reversed-phase-magnetic-field-generating-coil driving unit 327 is configured to amplify the input reversed-phase signal to a predetermined intensity, that is to carry out amplitude adjustment, based on the control signal input from the CPU 319. The amplified reversed-phase signal is output to the reversed-phase-magnetic-field generating coil 323.

The operation of the position detection apparatus 301 with the above-described structure will now be described.

In this embodiment, first, the CPU 319 outputs a control signal for setting the phase of the reversed-phase signal to be generated to be misaligned by substantially 180° to the phase adjusting unit 326. In addition the CPU 319 outputs a control signal for changing the amplitude of the reversed-phase signal to the reversed-phase-magnetic-field-generating-coil driving unit 327 every time measurement is carried out. In other words, while changing the intensity of the reversed-phase magnetic field, output signals associated with the combined magnetic field of the alternating magnetic field and the mutual magnetic field are obtained and stored in a memory 21.

The CPU 319 selects the amplification corresponding to the smallest signal intensity from the series of output signals obtained by changing the amplification and outputs a control signal for amplifying the reversed-phase signal with the selected amplification to the reversed-phase-magnetic-field-generating-coil driving unit 327. In addition, the CPU 319 outputs a control signal for changing the misalignment of the phase of the reversed-phase signal little by little from substantially 180° every time measurement is carried out. In other words, output signals associated with the combined magnetic field are obtained while changing the phase of the reversed-phase magnetic field and are stored in the memory 21.

Then, the CPU 319 selects the phase of an output signal having the weakest signal intensity among the output signals stored in the memory 21.

Subsequently, the position detection apparatus 301 amplifies the reversed-phase signal having a phase determined according to the procedure described above by the amplitude described above, and uses a reversed-phase magnetic field generated by this amplified reversed-phase signal.

The steps of generating an alternating magnetic field around the object 10 to be detected, detecting an induced magnetic field generated at the embedded coil 10a, and inputting the output signal associated with the combined magnetic field to the CPU 319 are the same as those in the first embodiment. Thus, descriptions thereof shall be omitted.

According to the structure described above, the CPU 319 can determine settings for the phase adjusting unit 326 and the reversed-phase-magnetic-field-generating-coil driving unit 327 that set the intensity of the combined magnetic field captured by the magnetic-field sensor 12 to a minimum value or substantially zero. Therefore, compared to determining these settings manually, the settings can be determined in a less amount of time.

Fifth Embodiment

A fourth embodiment of the present invention will be described below with reference to FIGS. 8 to 10.

The basic configuration of a medical magnetic inductance and position detection system according to this embodiment is the same as that in the first embodiment; however, the structures of the guidance-magnetic-field generating coil and the periphery thereof are different from those in the first embodiment. Thus, in this embodiment, only the structures of the guidance-magnetic-field generating coil and the periphery thereof shall be described with reference to FIGS. 8 to 10, and the description of the structures of other components shall be omitted.

Figure 8:
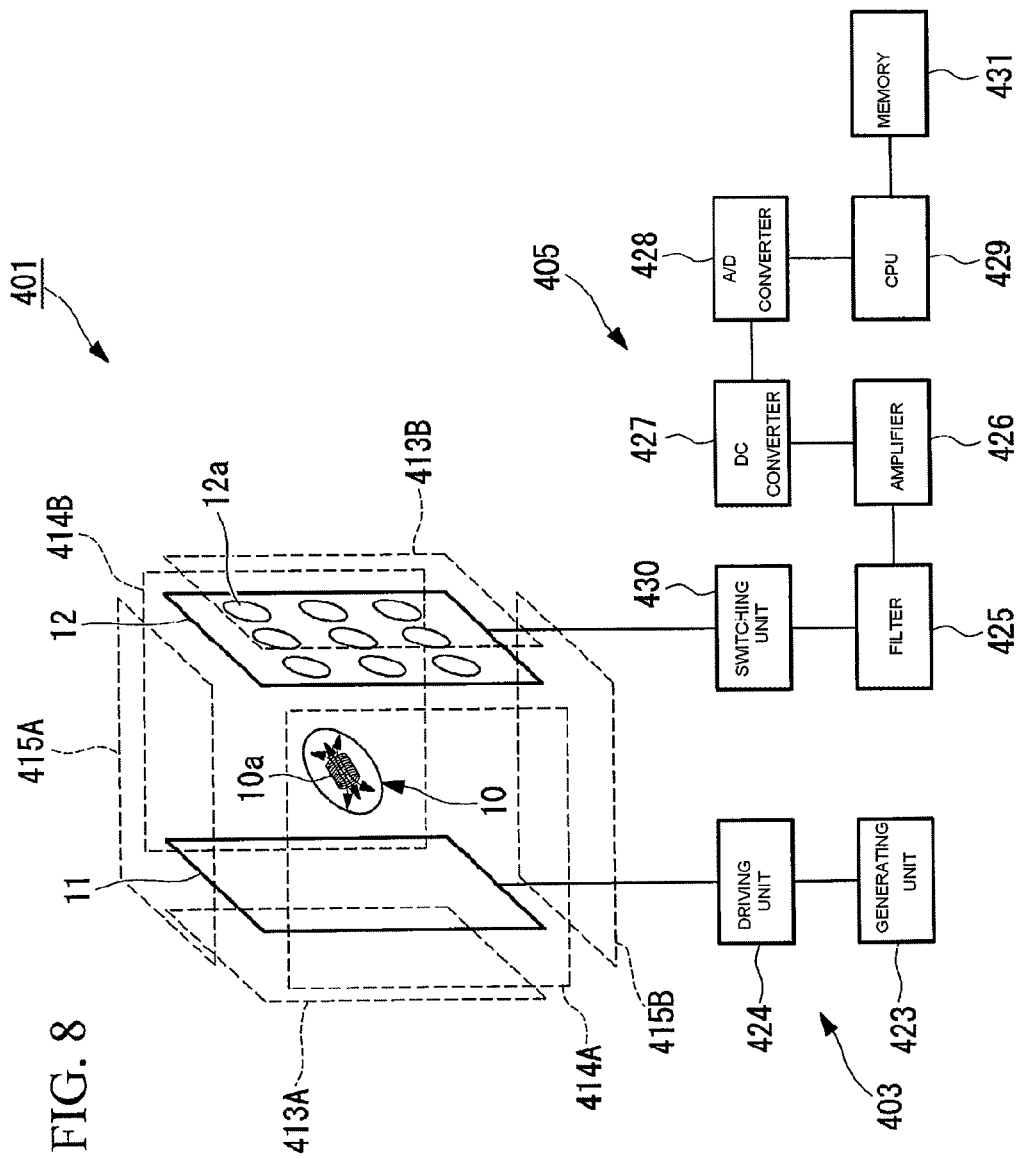
FIG. 8 is a schematic view illustrating the outline of a position detection apparatus according to a fifth embodiment of the present invention.

FIG. 8 is a schematic view illustrating the outline of the position detection apparatus according to this embodiment.

The same components as those in the first embodiment are denoted with the same reference numerals, and thus will not be described.

As shown in FIG. 8, a position detection apparatus 401 is mainly formed of a magnetic-field generating coil 11 that generates an alternating magnetic field; a magnetic-field sensor 12 that detects an induced magnetic field generated by an embedded coil 10a installed on an object 10 to be detected; and guidance-magnetic-field generating coils 413A, 413B, 414A, 414B, 415A, and 415B that generates an induced magnetic field for guiding the object 10 to be detected to a predetermined position in the body cavity.

A driving unit 403 for driving control of the magnetic-field generating coil 11 is provided on the magnetic-field generating coil 11, and a detecting unit 405 for processing a signal output from the magnetic-field sensor 12 is provided on the magnetic-field sensor 12.

The driving unit 403 is mainly composed of a signal generating unit 423 that outputs an alternating signal having a frequency of the alternating magnetic field generated at the magnetic-field generating coil 11 and a magnetic-field-generating-coil driving unit 424 that drives the magnetic-field generating coil 11 by amplifying the alternating signal input from the signal generating unit 423.

The detecting unit 405 is mainly composed of a filter 425 that cuts unwanted frequency components contained in an output signal from the detecting coils 12a; an amplifier 426 that amplifies the output signal from which unwanted components are cut; a DC converter 427 that converts the amplified output signal from an AC signal to a DC signal; an A/D converter 428 for converting the DC-converted output signal from an analog signal to a digital signal; a CPU 429 that performs computational processing based on the output signal converted into a digital signal; and a magnetic-field-sensor switching unit 430 that selects a predetermined output signal of the magnetic-field sensor 12 among all output signals from the magnetic-field sensor 12.

A memory 431 for saving an output signal acquired while the object 10 to be detected is not present is connected to the CPU 429. By arranging the memory 431, it is easier to subtract an output signal acquired while the object 10 to be detected is not present from an output signal acquired while the object 10 to be detected is present. For this reason, only an output signal associated with the induced magnetic field generated by the embedded coil 10a can easily be detected.

An example of the DC converter 427 is an RMS converter. However, the DC converter 427 is not limited and any known AC-DC converter may be used.

The guidance-magnetic-field generating coils 413A and 413B, the guidance-magnetic-field generating coils 414A and 414B, and the guidance-magnetic-field generating coils 415A and 415B are each disposed opposite to each other in a manner such as to satisfy Helmholtz conditions. Therefore, spatial intensity gradients are not generated in the magnetic fields generated by the guidance-magnetic-field generating coils 413A and 413B, the guidance-magnetic-field generating coils 414A and 414B, and the guidance-magnetic-field generating coils 415A and 415B, and uniform magnetic fields are generated within the induction range.

The central axes of the guidance-magnetic-field generating coils 413A and 413B, the guidance-magnetic-field generating coils 414A and 414B, and the guidance-magnetic-field generating coils 415A and 415B are each disposed so as to orthogonally intersect each other and are disposed in a manner such as to form a cubic spaces inside the coils. The cubic space is the operation space of the object 10 to be detected, as shown in FIG. 8.

Figure 9:
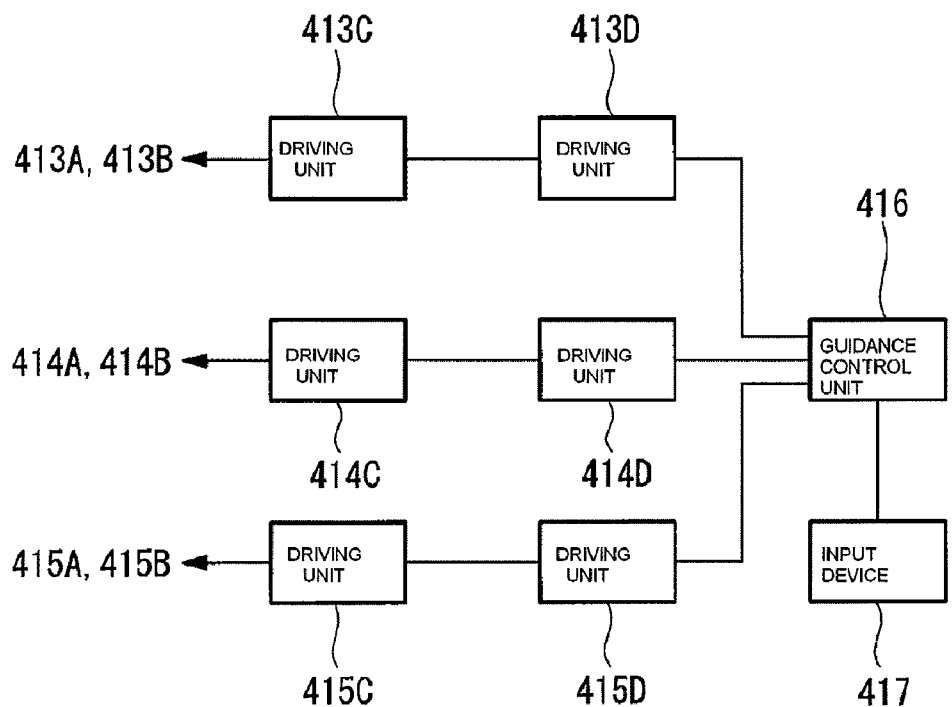
FIG. 9 is a block diagram showing the overall structure of a guidance magnetic-field generating coil shown in FIG. 8.

FIG. 9 is a block diagram illustrating the outline structure of the guidance-magnetic-field generating coils of FIG. 8. FIG. 10 is a circuit diagram illustrating the connection of the guidance-magnetic-field generating coils, shown in FIG. 9, and magnetic-field-generating-coil driving units.

For the pairs of the guidance-magnetic-field generating coils 413A and 413B, the guidance-magnetic-field generating coils 414A and 414B, and the guidance-magnetic-field generating coils 415A and 415B, the coils in each pair are electrically connected to each other.

Figure 10:
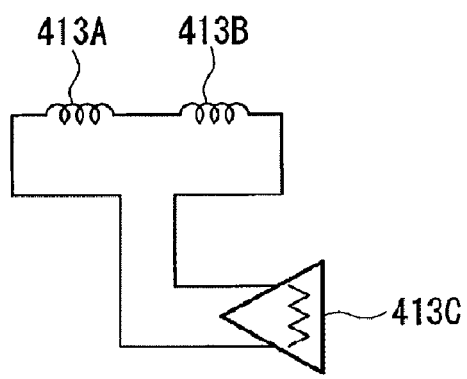
FIG. 10 is a circuit diagram illustrating the connection between a guidance-magnetic-field generating coil and guidance-magnetic-field-generating-coil driving unit.

As shown in FIGS. 9 and 10, guidance-magnetic-field-generating-coil driving units 413C, 414C, and 415C are electrically connected such that outputs thereof are input to the pairs of the guidance-magnetic-field generating coils 413A and 413B, the guidance-magnetic-field generating coils 414A and 414B, and the guidance-magnetic-field generating coils 415A and 415B, respectively. The guidance-magnetic-field-generating-coil driving units 413C, 414C, and 415C are electrically connected such that signals from signal generating units 413D, 414D, and 415D are input thereto, respectively. The signal generating units 413D, 414D, and 415D are electrically connected such that control signals from a guidance control unit 416 is input thereto. The guidance control unit 416 is electrically connected such that a signal from an input device 417 that receives an instruction for the guidance direction of the object 10 to be detected from the outside is input thereto.

The operation of position detection of the medical magnetic inductance and a position detection system 401 having the structure described above will now be described.

First, the operation of position detection of the object 10 to be detected by the medical magnetic inductance and a position detection system 401 will be described.

First, at the driving unit 403, as shown in FIG. 11, an AC signal having a predetermined frequency is generated in the signal generating unit 423, and the AC signal is output to the magnetic-field-generating-coil driving unit 424. The magnetic-field-generating-coil driving unit 424 amplifies the input AC signal to a predetermined intensity. The amplified AC signal is output to the magnetic-field generating coil 11. The magnetic-field generating coil 11 forms an alternating magnetic field therearound as a result of the AC signal being supplied.

When the magnetic flux of the alternating magnetic field intersects the object 10 to be detected, a resonant current with a predetermined frequency is induced in the object closed circuit having the embedded coil 10a installed therein. When a resonant current is induced in the object closed circuit, it causes the embedded coil 10a to form therearound an induced magnetic field having a predetermined frequency.

Since the magnetic fluxes of the above-described alternating magnetic field and the induced magnetic field intersect the magnetic-field sensor 12, the magnetic-field sensor 12 capture a magnetic flux generated by adding the magnetic fluxes of both the magnetic fields and generate an output signal that is an induced current based on a change in the intersecting magnetic fluxes. An output signal of the magnetic-field sensor 12 is output to the detecting unit 405.

In the detecting unit 405, the output signal that has been input is first input to the magnetic-field-sensor switching unit 430. The magnetic-field-sensor switching unit 430 passes only an output signal used for position detection of the object 10 to be detected therethrough and cuts out other output signals.

Examples of a method for selecting an output signal include selecting output signals with high signal intensity, output signals from the magnetic-field sensor 12 positioned near the object 10 to be detected, or the like.

Only an output signal used for position detection may be selected by arranging the magnetic-field-sensor switching unit 430 between the magnetic-field sensor 12 and the filter 425, as described above. Alternatively, by causing the magnetic-field-sensor switching unit 430 to switch the connection among a plurality of magnetic-field sensors 12, the output signals from all magnetic-field sensors 12 may be input to the detection section 405 in a time-division manner. Furthermore, by connecting the line between the filter 425 and the A/D converter 428 to a plurality of magnetic-field sensors 12, it is not necessary to use the magnetic-field-sensor switching unit 430 or select an output signal. Thus, no particular restrictions are applied.

The selected output signal is input to the filter 425, and frequency components in the output signal that are not used for position detection, for example, low-frequency components, are removed. The output signal from which unwanted components are removed is input to the amplifier 426 and is then amplified so as to have an input level appropriate for the A/D converter 428 downstream thereof.

The amplified output signal is input to the DC converter 427, and the output signal, which is an AC signal, is converted into a DC signal. Thereafter, the output signal is input to the A/D converter 428, and the output signal, which is an analog signal, is converted into a digital signal.

The output signal converted into a digital signal is input to the CPU 429. On the other hand, the output signal acquired from the memory 431 connected to the CPU 429 while the object 10 to be detected is not present is input to the CPU 429.

In the CPU 429, an output signal associated with the induced magnetic field is obtained by calculating the difference between both the output signals that have been input, and computation for identifying the position of the embedded coil 10a, namely the position of the object 10 to be detected, is carried out based on the obtained output signal associated with the induced magnetic field. For the computation for identifying the position, a known computation method can be used, and no particular restrictions are applied.

The operation of guiding the capsule medical device will now be described.

First, a movement that is to be applied to the object 10 to be detected for remote operation of the object 10 to be detected is input to an input device 417. The input device 417 outputs a signal to the guidance control unit 416 based on the input information. Based on the input signal, the guidance control unit 416 generates a control signal for generating a magnetic field for moving the object 10 to be detected, and outputs it to signal generating units 413D, 414D, and 415D.

In the signal generating units 413D, 414D, and 415D, signals output to the guidance-magnetic-field-generating-coil driving units 413C, 414C, and 415C are generated based on the input control signal. The guidance-magnetic-field-generating-coil driving units 413C, 414C, and 415C amplify the current of the input signals and cause the current to flow in the guidance-magnetic-field generating coils 413A and 413B, the guidance-magnetic-field generating coils 414A and 414B, and the guidance-magnetic-field generating coils 415A and 415B, respectively.

As described above, it is possible to generate an induced magnetic field in an area near the object 10 to be detected by causing electric current to flow in the guidance-magnetic-field generating coils 413A and 413B, the guidance-magnetic-field generating coils 414A and 414B, and the guidance-magnetic-field generating coils 415A and 415B. With this generated magnetic field, the magnet in the object 10 to be detected can be moved, and accordingly, the object 10 to be detected can be moved by moving the magnet.

The operation when a mutually induced magnetic field is generated by the guidance-magnetic-field generating coils 413A and 413B, the guidance-magnetic-field generating coils 414A and 414B, and the guidance-magnetic-field generating coils 415A and 415B, which is the main subject matter of the present invention, will now be described.

The guidance-magnetic-field generating coil 413A and the guidance-magnetic-field generating coil 413B, the guidance-magnetic-field generating coil 414A and the guidance-magnetic-field generating coil 414B, and the guidance-magnetic-field generating coil 415A and the guidance-magnetic-field generating coil 415B are electrically connected in series. Therefore, when the magnetic flux of the alternating magnetic field having varying magnetic field intensity intersects one of the guidance-magnetic-field generating coils 413A and 413B, one of the guidance-magnetic-field generating coils 414A and 414B, and one of the guidance-magnetic-field generating coils 415A and 415B, an induced electromotive force is generated in the coils through which the magnetic flux passes, i.e., an electromotive force that forms a magnetic field having a direction in which variations in the magnetic field intensity are cancelled out, namely, a reversed-phase magnetic field with a phase opposite to that of the above-described alternating magnetic field.

Since the guidance-magnetic-field generating coils 413A and 413B, the guidance-magnetic-field generating coils 414A and 414B, and the guidance-magnetic-field generating coils 415A and 415B are electrically connected in series to form closed circuits, an induced current based on the induced electromotive force generated at one of the pairs of coils is applied to the other coils of the guidance-magnetic-field generating coils 413A and 413B, the guidance-magnetic-field generating coils 414A and 414B, and the guidance-magnetic-field generating coils 415A and 415B.

When the induced current is applied to the other coils, the reversed-phase magnetic field is generated around the other coils.

Since the guidance-magnetic-field generating coils 413A, 413B, 414A, 414B, 415A, and 415B are normally set to have a low output impedance, the above-mentioned current based on induced electromotive force is applied and a magnetic field having a phase substantially opposite to the phase of the position-detection magnetic field can be generated.

Since the guidance-magnetic-field generating coils 413A, 413B, 414A, 414B, 415A, and 415B are connected in series to the two opposing guidance-magnetic-field generating coils 413A and 413B, there is an effect of canceling out even in the vicinity of the magnetic-field sensor 12, in the same way as in the first embodiment. For example, as shown in FIG. 8, the guidance-magnetic-field generating coil 413A functions as the coupled coil according to the first embodiment, and a magnetic field having a phase that is opposite to the position-detection magnetic field is generated also from the guidance-magnetic-field generating coil 413B connected in series with the guidance-magnetic-field generating coil 413A. In other words, without particularly providing a coupled coil and a reversed-phase-magnetic-field generating coil, the position-detection magnetic field generated in the vicinity of the magnetic-field sensor 12 can be canceled out by adjusting the positions of the coils.

The pair of position detecting coils may be combined with the guidance-magnetic-field generating coil pairs B and C.

Three pairs of position detecting coils, which is the same number of guidance-magnetic-field generating coils, may be positions so as to cancel out the position-detection magnetic field of the magnetic-field sensor unit.

According to the above-described structure, the position-detection magnetic-field generating coil 11 generates a position-detection magnetic field for inducing an induced magnetic field in the embedded coil 10a of the object 10 to be detected. The induced magnetic field generated by the embedded coil 10a is detected by the magnetic-field sensor 12 and is used to detect the position or orientation of the object 10 to be detected having the embedded coil 10a.

Furthermore, the induced magnetic fields generated by the three pairs of guidance-magnetic-field generating coils 413A and 413B, guidance-magnetic-field generating coils 414A and 414B, and guidance-magnetic-field generating coils 415A and 415B act on the magnet provided in the object 10 to be detected to control the position and orientation of the object 10 to be detected. Here, since the three pairs of guidance-magnetic-field generating coils 413A and 413B, guidance-magnetic-field generating coils 414A and 414B, and guidance-magnetic-field generating coils 415A and 415B are arranged such that the directions of their central axes are orthogonal to one another, the magnetic force lines of the induced magnetic fields can be oriented in any three-dimensional direction. As a result, the position and orientation of the object 10 to be detected including the magnet can be controlled three-dimensionally.

The technical field of the present invention is not limited to the aforementioned embodiments, and various modifications may be applied within the scope thereof without departing from the gist of the invention.

For example, in the embodiments described above, one of each of a magnetic-field generating unit, magnetic-field sensor, reversed-phase-magnetic-field generating coil, and so on are provided, and a configuration in which these are positioned on a substantially straight line is described. However, the structure is not limited, and a plurality of magnetic-field generating coil and so on may be provided, and these may be positioned on a plurality of straight lines. The number and position are not particularly limited.

What is claimed is:

1. A position detection apparatus comprising:
   a circuit provided inside an object to be detected, the circuit including at least one embedded coil;
   a first magnetic-field generating unit for generating a first magnetic field;
   a magnetic-field detecting unit for detecting an induced magnetic field generated at the embedded coil based on the first magnetic field; and
   a second magnetic-field generating unit for generating a second magnetic field having a phase substantially opposite to the phase of the first magnetic field,
   wherein the second magnetic-field generating unit includes a mutually-induced-magnetic-field generating coil for generating a mutually induced magnetic field based on the first magnetic field and a second magnetic-field generating coil for generating the second magnetic field,
   wherein the mutually-induced-magnetic-field generating coil is positioned in the vicinity of the first magnetic-field generating unit and the second magnetic-field generating coil is positioned in the vicinity of the magnetic-field detecting unit, and
   wherein the mutually-induced-magnetic-field generating coil and the second magnetic-field generating coil are electrically connected in series.

2. The position detection apparatus according to claim 1, wherein the second magnetic-field generating unit is provided with a moving mechanism for moving the position of at least one of the mutually-induced-magnetic-field generating coil and the second magnetic-field generating coil.

3. The position detection apparatus according to claim 2, wherein the moving mechanism moves the position of the mutually-induced-magnetic-field generating coil so as to minimize the intensity of a magnetic-field-intensity signal being output from the magnetic-field detecting unit and being associated with a combined magnetic field of the first magnetic field and the second magnetic field.

4. The position detection apparatus according to claim 2, wherein the moving mechanism moves the position of the second magnetic-field generating coil so as to minimize the intensity of a magnetic-field-intensity signal being output from the magnetic-field detecting unit and being associated with a combined magnetic field of the first magnetic field and the second magnetic field.

5. The position detection apparatus according to claim 1, wherein the second magnetic-field generating unit includes
   a phase adjusting unit for generating a signal having a substantially reversed phase from a signal for magnetic field generation,
   a second-magnetic-field-generating-coil driving unit for amplifying the signal.

6. The position detection apparatus according to claim 5, wherein the second-magnetic-field-generating-coil driving unit adjusts the intensity of the second magnetic field based on a magnetic-field-intensity signal output from the magnetic-field detecting unit so as to minimize the signal.

7. The position detection apparatus according to claim 1, further comprising:
   a display unit for displaying a magnetic-field-intensity signal output form the magnetic-field detecting unit.

8. The position detection apparatus according to claim 1, wherein the magnetic-field detecting unit and the second magnetic-field generating unit are arranged on substantially the same flat surface.

9. The position detection apparatus according to claim 1, wherein the object to be detected is a capsule medical device.

10. The position detection apparatus according to claim 9, wherein the capsule medical device includes a container for holding medication to be administered to a subject.

11. The position detection apparatus according to claim 1, wherein the second magnetic-field generating unit is provided with a moving mechanism for moving a position of at least one of the mutually-induced-magnetic-field generating coil and the second magnetic-field generating coil.

12. The position detection apparatus according to claim 11, wherein the moving mechanism moves the position of the mutually-induced-magnetic-field generating coil so as to minimize the intensity of a magnetic-field intensity signal being output from the magnetic-field detecting unit and being associated with a combined magnetic field of the first magnetic field and the second magnetic field.

13. The position detection apparatus according to claim 1, wherein the object to be detected is a tubular medical device.

14. The position detection apparatus according to claim 13, wherein the tubular medical device is a catheter or an endoscope.

15. The position detection apparatus according to claim 13, wherein the embedded coil is provided substantially at a tip of the tubular medical device.

16. The position detection apparatus according to claim 13, wherein the embedded coil is provided at an intermediate section of the tubular medical device.

17. The position detection apparatus according to claim 1, wherein the mutually-induced-magnetic-field generating coil and the first magnetic-field generating unit are arranged on substantially the same flat surface.

18. The position detection apparatus according to claim 2, wherein the moving mechanism includes a moving rail and a supporting part disposed so as to be slidable on the moving rail.

19. The position detection apparatus according to claim 18, wherein the moving rail is positioned substantially orthogonal to a surface of a magnetic sensor.

20. The position detection apparatus according to claim 5, wherein the phase adjusting unit adjusts the phase of the reversed-phase signal on the basis of the magnetic-field-intensity signal output from the magnetic-field detecting unit so as to minimize the signal thereof.

21. The position detection apparatus according to claim 20, wherein the phase adjusting unit
 includes a memory for storing, in association with the phase of the reversed-phase signal, the signal being output while changing the phase of the reversed-phase signal and being detected by the magnetic-field detecting unit, and
 adjusts the phase of the reversed-phase signal based on information stored in the memory.

22. The position detection apparatus according to claim 6, wherein the second-magnetic-field-generating-coil driving unit
 includes a memory for storing, in association with the second magnetic field intensity, the signal intensity being output while changing the second magnetic field intensity and being detected by the magnetic-field detecting unit, and adjusts the second magnetic field intensity based on information stored in the memory.

23. The position detection apparatus according to claim 9, wherein the capsule medical device includes an image-acquisition unit.

24. A method for detecting at least one of a position and an orientation of an object to be detected, comprising:
 generating a first magnetic field by using a first magnetic-field generating unit;
 detecting, by using a magnetic-field detecting unit, an induced magnetic field when an embedded coil that is embedded in the object to be detected receives the first magnetic field; and
 generating a second magnetic field having a phase substantially opposite to the phase of the first magnetic field by using a second magnetic-field generating unit,
 wherein the second magnetic-field generating unit includes a mutually-induced-magnetic-field generating coil for generating a mutually induced magnetic field based on the first magnetic field and a second magnetic-field generating coil for generating the second magnetic field,
 wherein the mutually-induced-magnetic-field generating coil is positioned in the vicinity of the first magnetic-field generating unit and the second magnetic-field generating coil is positioned in the vicinity of the magnetic-field detecting unit, and
 wherein the mutually-induced-magnetic-field generating coil and the second magnetic-field generating coil are electrically connected in series.

25. The method according to claim 24, further comprising:
 minimizing a magnetic field intensity of the detected induced magnetic field by adjusting the opposite-phase magnetic field;
 generating the induced magnetic field when an embedded coil that is embedded in the object to be detected receives the first magnetic field.

26. The method according to claim 25, including minimizing the magnetic field intensity by changing a phase of the opposite-phase magnetic field.

27. The method according to claim 25, including minimizing the magnetic field intensity by changing an intensity of the opposite-phase magnetic field.

28. The method according to claim 25, including minimizing the magnetic field intensity by changing a positional relationship between the magnetic-field detecting unit and the second magnetic-field generating unit.

29. The method according to claim 25, including minimizing the magnetic field intensity by changing a positional relationship between the second magnetic-field generating unit and the first magnetic-field generating unit.

30. A medical-device-position detection system comprising:
 a medical device including a circuit having at least one embedded coil, and a magnet;
 a first magnetic-field generating unit for generating a first magnetic field;
 a magnetic-field detecting unit for detecting an induced magnetic field excited at the embedded coil by the first magnetic field; and
 a second magnetic-field generating unit for generating a second magnetic field having a phase substantially opposite to the phase of the first magnetic field,
 wherein the position and orientation of the magnet included in the medical device is controlled based on the second magnetic field generated by the second magnetic-field generating unit.

* * * * *